(12) United States Patent
Chang et al.

(10) Patent No.: US 7,700,785 B2
(45) Date of Patent: Apr. 20, 2010

(54) PROCESS FOR PREPARATION OF DIALKYL CARBONATE

(75) Inventors: Chih-Wei Chang, Taichung (TW); Chia-Jung Tsai, Taipei (TW); Ying-Tien Chen, Taipei (TW)

(73) Assignee: China Petrochemical Development Corporation, Taipei (TW)

( * ) Notice: Subject to any disclaimer, the term of this patent is extended or adjusted under 35 U.S.C. 154(b) by 17 days.

(21) Appl. No.: 12/009,101

(22) Filed: Jan. 15, 2008

(65) Prior Publication Data

US 2008/0214856 A1    Sep. 4, 2008

(30) Foreign Application Priority Data

Jan. 17, 2007    (TW) .............................. 96101693 A

(51) Int. Cl.
    C07D 233/66    (2006.01)
    C07D 237/10    (2006.01)
(52) U.S. Cl. .................................... 548/335.1; 544/224
(58) Field of Classification Search ............. 548/335.1, 548/343.1; 544/224
    See application file for complete search history.

(56) References Cited

U.S. PATENT DOCUMENTS

| | | | |
|---|---|---|---|
| 2,331,386 A | 10/1943 | Gaylor | |
| 3,114,762 A | 12/1963 | Mador et al. | |
| 3,227,740 A | 1/1966 | Fenton | |
| 3,846,468 A | 11/1974 | Perrotti et al. | |
| 3,980,690 A | 9/1976 | Cipriani et al. | |
| 4,113,762 A | 9/1978 | Gaenzler et al. | |
| 4,218,391 A | 8/1980 | Cipriani et al. | |
| 4,318,862 A | 3/1982 | Roman et al. | |
| 4,360,477 A | 11/1982 | Hallgren et al. | |
| 4,370,275 A * | 1/1983 | Stammann et al. | ........... 558/277 |
| 4,761,467 A * | 8/1988 | Bhattacharya | ............... 558/277 |
| 5,151,541 A * | 9/1992 | Joerg et al. | .................. 558/277 |
| 5,162,563 A | 11/1992 | Nishihara et al. | |

FOREIGN PATENT DOCUMENTS

| | | | |
|---|---|---|---|
| CN | 1197792 | | 11/1998 |
| CN | 1333086 | * | 1/2002 |
| CN | 1333086 A | | 1/2002 |
| EP | 0460732 | | 12/1991 |
| JP | 54-24827 | | 12/1975 |

OTHER PUBLICATIONS

Rivetti et al., J. Organometallic Chem, 174, 221-226 (1979) (abstract only).

* cited by examiner

*Primary Examiner*—Rei-Tsang Shiao
*Assistant Examiner*—Janet L Coppins
(74) *Attorney, Agent, or Firm*—Edwards Angell Palmer & Dodge LLP; Peter F. Corless; Dwight D. Kim

(57) ABSTRACT

Provided is a process for preparation of dialkyl carbonates, comprising the step of performing oxidative carbonylation of an alcohol in liquid phase in the presence of CO and $O_2$, to form dialkyl carbonate in a catalyst system comprising a metal halide as catalyst and at least one nitrogen-containing compound selected from the group consisting of imidazole derivatives (excluding unsubstituted imidazole), benzoimidazole derivatives, pyridazine derivatives, carbazole, acridine and non-cyclic amines as auxiliary catalyst. The process of the invention, by using above catalyst system, can increase the conversion ratio of alcohol and the selectivity of the oxidative carbonylation reaction, thus increasing the total yield of dialkyl carbonate. In addition, the process of the invention has the advantages of reducing the required amount of the catalyst and causing less corrosion to the reactor.

12 Claims, No Drawings

PROCESS FOR PREPARATION OF DIALKYL CARBONATE

FIELD OF THE INVENTION

The invention relates to processes for preparation of dialkyl carbonate by using alcohol as starting material, and more particularly, to a process for preparation of dialkyl carbonate by oxidative carbonylation of alcohol.

BACKGROUND OF THE INVENTION

Dimethyl carbonate is an extremely versatile product which finds use as an organic solvent or a reactant (a substitute for phosgene) in the synthesis of other alkyl or aryl carbonates, which are useful as synthetic lubricants, solvents, plasticizers and monomers for organic glasses, and in reactions of methylation and carbonylation for preparing isocyanates, polyurethanes and polycarbonates. Dimethyl carbonate also has other applications. For example, U.S. Pat. No. 2,331,386 discloses the use of dimethyl carbonate or other organic carbonates, or a mixture of organic carbonate and ether (especially methyl t-butyl ether) as an anti-explosive additive for gasoline or fuels heavier than gasoline.

Conventionally, dimethyl carbonate is synthesized by phosgenation of methanol (phosgene route). However, since phosgene is a toxic chemical and causes corrosion to the reactor, the phosgene route has been gradually replaced by oxidative carbonylation of methanol (oxidative carbonylation route) in recent years. Compared with the phosgene route, the oxidative carbonylation route has advantages of easy acquirement of starting materials, simple synthetic procedures, less environmental pollution and lower production cost.

Oxidative carbonylation of methanol can be performed in a vapor phase or a liquid phase, issued in the patents by Ube Industries, Ltd, Japan and Enichem, respectively. One representative example of gas-phase oxidative carbonylation of methanol is the process disclosed by U.S. Pat. No. 5,162,563 issued to Ube Industries, Ltd, Japan., which comprises bringing carbon monoxide into contact with an ester of nitrous acid in a vapor phase in the presence of a solid catalyst, for example, $PdCl_2$ combined with copper.

Oxidative carbonylation of methanol can also be performed in a liquid phase. Various catalysts or catalyst systems have been proposed for use in liquid-phase oxidative carbonylation of methanol. For example, EP0460732 issued to Enichem Industries, Ltd. discloses a copper catalyst such as cuprous chloride (CuCl). U.S. Pat. Nos. 4,218,391 and 4,318,862 disclose catalyst comprising a salt of a metal belonging to the Groups IB, IIB and VIIIB of the Periodic Table, preferably the salts of monovalent copper (for example CuCl and CuBr). In the processes of these patents, in order to increase reaction rate, it is necessary to use high concentrations of cuprous chloride; however, such high concentrations of cuprous chloride may cause corrosion to the reactor. To resolve this issue, Enichem used a reactor with a glass liner on its inner wall. However, the presence of glass liner would enlarge the reactor, which was undesirable from the viewpoint of space utilization.

Chinese Patent No. CN1197792 discloses a two-component catalyst system comprising cuprous chloride as catalyst and one inorganic salt such as $MgCl_2$, $CaCl_2$, $ZnCl_2$, KCl etc. as catalyst promoter. Japanese Patent No. 54-24827 discloses a similar two-component catalyst system including cuprous halide as catalyst and a halide of alkali metal or alkaline earth metal as catalyst promoter. Although these two-component catalyst systems can increase the solubility of CuCl in the reaction medium, they still have the problem of causing corrosion to the reactor.

U.S. Pat. No. 3,846,468 discloses catalyst consisting of cuprous chloride complexed with an organic ligand selected from the group consisting of pyridine, dipyridyl, imidazole, phenanthroline, alkyl or aryl phosphines, dimethylsulfoxide, dimethylformamide, quinuclidine, $CH_3CN$, $C_6H_5CN$, malonitrile, succinonitrile and adiponitrile. In Rivetti et al., J. Organometallic Chem, 174, 221-226 (1979), a metal complex is also used as catalyst, wherein the catalyst consisting of Pd complexed with an organic and reports that Pd complexed with a tertiary amine would increase the yield of dimethyl carbonate, while Pd complexed with an alkyl phosphine would inhibit all carbonylation of methanol. U.S. Pat. No. 4,113,762 discloses a copper-containing catalyst comprising a complex formed between cuprous chloride and vanadium trichloride, chromium trichloride, iron trichloride, cobalt-II-chloride, aluminum trichloride, or silicon tetrachloride. U.S. Pat. No. 3,980,690 discloses catalyst consisting of a complex of copper chloride and poly-4-vinylpyridine.

U.S. Pat. No. 3,114,762 discloses adding cobalt- or palladium-containing salts and bromide salts into iron or copper oxidants containing the same anion. U.S. Pat. No. 3,227,740 discloses using mercury halides or carboxylates as catalysts. U.S. Pat. No. 4,360,477 discloses a process for preparation of dialkyl carbonate by using cupric chloride ($CuCl_2$) or cupric bromide ($CuBr_2$) as catalysts. U.S. Pat. No. 4,370,275 discloses catalyst comprising as the essential components, copper and/or copper ions, one or more anions selected from oxide anion, hydroxide anion and carbonate anion, halide ions, and one or more nitrogen bases. In case that a typical catalyst containing Cu(II)O, Cu(II)$Cl_2$ and pyridine HCl was used, the methanol was converted into dialkyl carbonate to the extent of 7.7%.

U.S. Pat. No. 4,761,467 discloses catalyst system containing Cu(OMe)Cl as catalyst and a pyridine compound (for example, pyridine, 2,2'-diprimidyl, 4-methyoxypyridine, 2-(methylthio)pyridine, 4-(morpholino)pyridine, 4-(N-methylpiperazine) pyridine, 2-pyridyl-2'-pyrimidiyl, pentachloropyridine) as a ligand of the catalyst. U.S. Pat. No. 5,151,541 discloses a process for preparation of dialkyl carbonate by using a copper catalyst (for example, Cu(OMe)Cl and Cu(OMe)Br) and a co-solvent selected from cyclic ureas (for example dimethylethylene urea and/or dimethylpropylene urea). Chinese Patent No. 1333086A discloses a cuprous chloride complex as catalyst and nitrogen-containing compounds (such as pyridine, imidazole aminopyridine, polypyridine, 4-phenylpyridine, N-methyl-pyrrolidone) or nitrogen-containing polymer (such as polyethylene pyridine, polyethylene pyrrolidone) as a ligand of the catalyst. The previous processes using any of the above catalysts are still not satisfactory because of low yield and/or the problem of corrosion to the reactor due to using large amount of catalysts.

SUMMARY OF THE INVENTION

In view of the above problems, it is therefore an objective of the invention is to provide a process for preparation of dialkyl carbonate with a high conversion ratio of alcohol.

It is another objective of the invention is to provide a process for preparation of dialkyl carbonate with high reaction selectivity.

It is still another objective of the invention is to provide a process for preparation of dialkyl carbonate with high reactivity.

It is yet another objective of the invention to provide a process for preparation of dialkyl carbonate, which causes less corrosion to the reactor.

In order to achieve the above and other objectives, the invention provides a process for preparation of dialkyl carbonate, comprising oxidative carbonylation of an alcohol in a liquid phase in the presence of CO and $O_2$, to form dialkyl carbonate, wherein catalyst system comprising a metal halide as catalyst and at least one nitrogen-containing compound as auxiliary catalyst is used, said nitrogen-containing compound is selected from the group consisting of imidazole derivatives (excluding unsubstituted imidazole), benzoimidazole derivatives, pyridazine derivatives, carbazole, acridine and non-cyclic amines. The process of the invention, by using the above catalyst system, can increase the conversion ratio of the alcohol and selectivity of the oxidative carbonylation reaction, thus increasing the total yield of dialkyl carbonate. In addition, the process of the invention has the advantages of reducing the required amount of the catalyst and causing less corrosion to the reactor.

DETAILED DESCRIPTION OF THE INVENTION

The invention provides a process for preparation of dialkyl carbonate, comprising oxidative carbonylation of an alcohol in a liquid phase in the presence of CO and $O_2$, to form dialkyl carbonate, wherein catalyst system comprising a metal halide as catalyst and at least one nitrogen-containing compound as auxiliary catalyst is used. The process can use a five-membered heterocyclic compound having two nitrogen atoms, a benzo-five-membered heterocyclic compound having two nitrogen atoms, a six-membered heterocyclic compound having two nitrogen atoms or a fused cyclic compound having nitrogen atoms as the auxiliary catalyst.

In the first embodiment, a five-membered heterocyclic compound having two nitrogen atoms is used as auxiliary catalyst. For example, the imidazole derivative represented by formula (I) below is used.

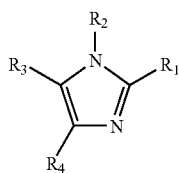

(I)

wherein $R^1$, $R^2$, $R^3$ and $R^4$ are independently selected from the group consisting of hydrogen, halogen, cyano, amino, $C_{1-6}$ alkylamino, $C_{1-12}$ alkyl, $C_{1-12}$ alkoxy, $C_{1-12}$ alkanoyl, $C_{3-12}$ cycloalkyl, $C_{3-12}$ cycloalkyloxy, $C_{3-12}$ cycloalkylacyl, $C_{6-20}$ aryl, $C_{7-20}$ aralkyl and $C_{7-20}$ alkylaryl; wherein $C_{1-6}$ alkylamino, $C_{1-12}$ alkyl, $C_{1-12}$ alkoxy, $C_{1-12}$ alkanoyl, $C_{3-12}$ cycloalkyl, $C_{3-12}$ cycloalkyloxy, $C_{3-12}$ cycloalkylacyl, $C_{6-20}$ aryl, $C_{7-20}$ aralkyl and $C_{7-20}$ alkylaryl may be further substituted by halogen, nitro or cyano. The preferred examples of the imidazole derivatives represented by formula (I) include, but are not limited to, 2-methylimidazole, 1-methylimidazole, N-acetylimidazole, 2-isopropylimidazole, 1-(4-nitrophenyl)imidazole or 4,5-diphenylimidazole.

In the second embodiment, a benzo-five-membered heterocyclic compound having two nitrogen atoms is used as auxiliary catalyst. For example, the benzoimidazole derivative represented by formula (II) below is used.

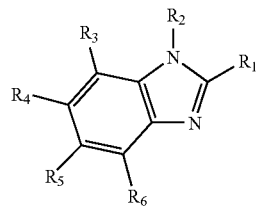

(II)

wherein $R^1$, $R^2$, $R^3$, $R^4$, $R^5$ and $R^6$ are independently selected from the group consisting of hydrogen, halogen, nitro, cyano, amino, $C_{1-6}$ alkylamino, $C_{1-12}$ alkyl, $C_{1-12}$ alkoxy, $C_{1-12}$ alkanoyl, $C_{3-12}$ cycloalkyl, $C_{3-12}$ cycloalkyloxy, $C_{3-12}$ cycloalkylacyl, $C_{6-20}$ aryl, $C_{7-20}$ aralkyl and $C_{7-20}$ alkylaryl; wherein $C_{1-6}$ alkylamino, $C_{1-12}$ alkyl, $C_{1-12}$ alkoxy, $C_{1-12}$ alkanoyl, $C_{3-12}$ cycloalkyl, $C_{3-12}$ cycloalkyloxy, $C_{3-12}$ cycloalkylacyl, $C_{6-20}$ aryl, $C_{7-20}$ aralkyl and $C_{7-20}$ alkylaryl may be further substituted by halogen, nitro or cyano. The preferred examples of the benzoimidazole derivative of formula (II) include, but are not limited to, 2-methylbenzoimidazole or 2-aminobenzoimidazole.

In the third embodiment, a six-membered heterocyclic compound having two nitrogen atoms is used as auxiliary catalyst. For example, the pyridazine derivative represented by formula (III) below is used.

(III)

wherein $R^1$, $R^2$, $R^3$ and $R^4$ are independently selected from the group consisting of hydrogen, halogen, nitro, cyano, amino, $C_{1-6}$ alkylamino, $C_{1-12}$ alkyl, $C_{1-12}$ alkoxy, $C_{1-12}$ alkanoyl, $C_{3-12}$ cycloalkyl, $C_{3-12}$ cycloalkyloxy, $C_{3-12}$ cycloalkylacyl, $C_{6-20}$ aryl, $C_{7-20}$ aralkyl and $C_{7-20}$ alkylaryl; wherein $C_{1-6}$ alkylamino, $C_{1-12}$ alkyl, $C_{1-12}$ alkoxy, $C_{1-12}$ alkanoyl, $C_{3-12}$ cycloalkyl, $C_{3-12}$ cycloalkyloxy, $C_{3-12}$ cycloalkylacyl, $C_{6-20}$ aryl, $C_{7-20}$ aralkyl and $C_{7-20}$ alkylaryl may be further substituted by halogen, nitro or cyano.

In the fourth embodiment, a fused cyclic compound having nitrogen atoms is used as auxiliary catalyst. The preferred examples of the fused cyclic compound include, but are not limited to carbazole or acridine.

The method of the invention can also use a compound having nitrogen atoms as auxiliary catalyst, for example, the structure represented by formula (IV) below.

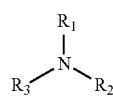

(IV)

wherein $R^1$, $R^2$ and $R^3$ are independently selected from the group consisting of hydrogen, halogen, nitro, cyano, amino, $C_{1-6}$ alkylamino, $C_{1-12}$ alkyl, $C_{1-12}$ alkoxy, $C_{1-12}$ alkanoyl, $C_{3-12}$ cycloalkyl, $C_{3-12}$ cycloalkyloxy, $C_{3-12}$ cycloalkylacyl, $C_{6-20}$ aryl, $C_{7-20}$ aralkyl and $C_{7-20}$ alkylaryl; wherein $C_{1-6}$ alkylamino, $C_{1-12}$ alkyl, $C_{1-12}$ alkoxy, $C_{1-12}$ alkanoyl, $C_{3-12}$ cycloalkyl, $C_{3-12}$ cycloalkyloxy, $C_{3-12}$ cycloalkylacyl, $C_{6-20}$ aryl, $C_{7-20}$ aralkyl and $C_{7-20}$ alkylaryl may be further substituted by halogen, nitro or cyano. The preferred examples of the non-cyclic amine of formula (IV) include, but are not limited to triphenylamine.

The "metal" in the metal halide catalyst includes the ions of the metals of Groups IB, IIB and VIIIB in the Periodic Table, for example Cu(I), Cu(II), Vc(III), Cr(III), Fe(III), Co(II), Al(III) or Si(IV), preferably Cu(I) and Cu(II). In a preferred embodiment, Cu(I)Cl or Cu(II)Cl$_2$ are used as metal halide catalysts. The concentration of the metal halide catalyst is usually in the range of 1 to 50000 ppm, and preferably in the range of 2000 to 30000 ppm. In general, the molar ratio of the metal halide catalyst to the auxiliary catalyst is in the range of 10:1 to 1:10, and preferably in the range of 5:1 to 1:5. The reaction temperature is usually in the range of 60 to 200, and preferably in the range of 90 to 180; the reaction pressure is usually 15 to 40 kg/cm$^2$, and preferably in the range of 15 to 40 kg/cm$^2$.

The features and the effects of the invention are further illustrated by the specific examples, but these examples are not constructed as a limit to the scope of the invention.

EXAMPLE

The conversion ratio, the selectivity and the yield in the Examples are calculated as follows:

Conversion ratio (%)=consumed methanol (mol)/
methanol feed (mol)×100%

Selectivity (%)=2×produced DMC (mol)/consumed
methanol (mol)×100%

Yield (%)=conversion ratio (%)×selectivity
(%)×100%

Comparative Example 1

An amount of 228.5 g of methanol (7.14 mol) and Cu(I)Cl (5000 ppm calculated as Cu) were fed to a IL stainless steel-made, Teflon-lined, high pressure reactor provided with a stirrer. The air in the reactor was replaced with nitrogen gas. After the reaction system was pressed with nitrogen to 25 kg/cm$^2$ and heated to 120, a mixture of carbon monoxide and oxygen gas (the volume ratio of O$_2$/CO is 6/94) was fed to the reactor at a rate of 645 ml/min, while the pressure of the reactor was maintained at 25 kg/cm$^2$. After the reaction was performed for 80 min., the product was analyzed by gas chromatography and the conversion ratio, the selectivity and the yield were calculated. The results were shown in Table 1.

Comparative Example 2

An amount of 228.5 g of methanol (7.14 mol) and Cu(II)Cl$_2$ (5000 ppm calculated as Cu) were fed to a 1 L stainless steel-made, Teflon-lined, high pressure reactor provided with a stirrer. The air in the reactor was replaced with nitrogen gas. After the reaction system was pressed with nitrogen to 25 kg/cm$^2$ and heated to 120, a mixture of carbon monoxide and oxygen gas (the volume ratio of O$_2$/CO is 6/94) was fed to the reactor at a rate of 645 ml/min, while the pressure of the reactor was maintained at 25 kg/cm$^2$. After the reaction was performed for 80 min., the product was analyzed by gas chromatography and the conversion ratio, the selectivity and the yield were calculated. The results were shown in Table 1.

Example 1

The procedures of Comparative Example 1 were repeated except using 2-methylimidazole as auxiliary catalyst with a molar ratio of 2-methylimidazole to copper halide of 2:1. The product was analyzed by gas chromatography and the conversion ratio, the selectivity and the yield were calculated. The results were shown in Table 1.

Examples 2 to 7

The procedures of Example 1 were repeated except using the different auxiliary catalysts as shown in Table 1. The product was analyzed by gas chromatography and the conversion ratio, the selectivity and the yield were calculated. The results were shown in Table 1.

TABLE 1

| | Catalyst | Auxiliary Catalyst | Conversion ratio | Selectivity | Yield |
|---|---|---|---|---|---|
| Comparative Example 1 | Cu(I)Cl | — | 10.6 | 74.4 | 7.9 |
| Comparative Example 2 | Cu(II)Cl$_2$ | — | 5.0 | 73.7 | 3.7 |
| Example 1 | Cu(I)Cl | 2-methylimidazole | 13.6 | 98.2 | 13.4 |
| Example 2 | Cu(I)Cl | N-acetylimidazole | 16.0 | 80.4 | 12.9 |
| Example 3 | Cu(I)Cl | 1-methylimidazole | 14.5 | 64.2 | 9.3 |
| Example 4 | Cu(II)Cl$_2$ | 2-methylimidazole | 10.2 | 95.9 | 9.8 |
| Example 5 | Cu(I)Cl | 1-(4-nitrophenyl) imidazole | 12.8 | 84.2 | 10.8 |
| Example 6 | Cu(I)Cl | carbazole | 9.4 | 85.8 | 8.1 |
| Example 7 | Cu(I)Cl | pyridazine | 11.7 | 77.6 | 9.1 |

Example 8

The procedures of Example 1 were repeated except Cu(I)Cl was replaced with Cu(I)Br. The product was analyzed by gas chromatography and the conversion ratio, the selectivity and the yield were calculated. The results were shown in Table 2.

Example 9

The procedures of Example 8 were repeated except 2-methylimidazole was replaced with N-acetylimidazole. The product was analyzed by gas chromatography and the conversion ratio, the selectivity and the yield were calculated. The results were shown in Table 2.

TABLE 2

| | Catalyst | Auxiliary Catalyst | Conversion ratio | Selectivity | Yield |
|---|---|---|---|---|---|
| Comparative Example 1 | Cu(I)Cl | — | 10.6 | 74.4 | 7.9 |
| Example 1 | Cu(I)Cl | 2-methylimidazole | 13.6 | 98.2 | 13.4 |
| Example 8 | Cu(I)Br | 2-methylimidazole | 12.1 | 85.1 | 10.3 |
| Example 9 | Cu(I)Br | N-acetylimidazole | 15.4 | 82.5 | 12.7 |

Example 10

The procedures of Example 1 were repeated except the reaction system was pressured with nitrogen gas to 20 kg/cm$^2$. The product was analyzed by gas chromatography and the conversion ratio, the selectivity and the yield were calculated. The results were shown in Table 3.

Example 11

The procedures of Example 1 were repeated except the reaction system was pressured with nitrogen gas to 30 kg/cm². The product was analyzed by gas chromatography and the conversion ratio, the selectivity and the yield were calculated. The results were shown in Table 3.

TABLE 3

| | Reaction Pressure (kg/cm²) | Auxiliary Catalyst | Conversion ratio | Selectivity | Yield |
|---|---|---|---|---|---|
| Comparative Example 1 | 25 | — | 10.6 | 74.4 | 7.9 |
| Example 1 | 25 | 2-methylimidazole | 13.6 | 98.2 | 13.4 |
| Example 10 | 20 | 2-methylimidazole | 14.0 | 82.9 | 11.6 |
| Example 11 | 30 | 2-methylimidazole | 14.9 | 86.5 | 12.9 |

Example 12

The procedures of Example 1 were repeated except the amount (calculated as Cu) of Cu(I)Cl was changed to 10000 ppm. The product was analyzed by gas chromatography and the conversion ratio, the selectivity and the yield were calculated. The results were shown in Table 4.

Example 13

The procedures of Example 1 were repeated except the amount (calculated as Cu) of Cu(I)Cl was changed to 20000 ppm. The product was analyzed by gas chromatography and the conversion ratio, the selectivity and the yield were calculated. The results were shown in Table 4.

TABLE 4

| | Amount (calculated as Cu) of Cu(I)Cl (ppm) | Auxiliary Catalyst | Conversion ratio | Selectivity | Yield |
|---|---|---|---|---|---|
| Comparative Example 1 | 5000 | — | 10.6 | 74.4 | 7.9 |
| Example 1 | 5000 | 2-methyl-imidazole | 13.6 | 98.2 | 13.4 |
| Example 12 | 10000 | 2-methyl-imidazole | 14.9 | 94.1 | 14.0 |
| Example 13 | 20000 | 2-methyl-imidazole | 15.4 | 95.5 | 14.7 |

Example 14

The procedures of Example 7 were repeated except the molar ratio of auxiliary catalyst to Cu(I)Cl was changed to 1:1. The product was analyzed by gas chromatography and the conversion ratio, the selectivity and the yield were calculated. The results were shown in Table 5.

TABLE 5

| | Catalyst | Molar ratio of Auxiliary Catalyst/catalyst | Conversion ratio | Selectivity | Yield |
|---|---|---|---|---|---|
| Comparative Example 1 | Cu(I)Cl | — | 10.6 | 74.4 | 7.9 |
| Example 7 | Cu(I)Cl | 2/1 | 11.7 | 77.6 | 9.1 |
| Example 14 | Cu(I)Cl | 1/1 | 9.6 | 89.6 | 8.6 |

From the Tables 1 to 5, it can be observed that by using the catalyst system comprising a metal halide as catalyst and the specified nitrogen-containing compound as auxiliary catalyst, the conversion ratio of methanol, the selectivity of oxidative carbonylation reaction and the yield of dimethyl carbonate can be significantly increased.

What is claimed is:

1. A process for preparation of dialkyl carbonate, comprising the step of:
performing oxidative carbonylation of an alcohol in liquid phase in the presence of CO and $O_2$ to form dialkyl carbonate in a catalyst system comprising a metal halide as catalyst and at least one auxiliary catalyst, wherein the auxiliary catalyst is selected from the group consisting of:
imidazole derivative of formula (I):

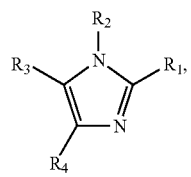

(I)

wherein $R_1$, $R_2$, $R_3$ and $R_4$ are independently selected from the group consisting of hydrogen, halogen, cyano, amino, $C_{1-6}$ alkylamino, $C_{1-12}$ alkyl, $C_{1-12}$ alkoxy, $C_{1-12}$ alkanoyl, $C_{3-12}$ cycloalkyl, $C_{3-12}$ cycloalkyloxy, $C_{3-12}$ cycloalkylacyl, $C_{6-20}$ aryl $C_{7-20}$ aralkyl and $C_{7-20}$ alkylaryl; wherein $C_{1-6}$ alkylamino, $C_{1-12}$ alkyl, $C_{1-12}$ alkoxy, $C_{1-12}$ alkanoyl, $C_{3-12}$ cycloalkyl, $C_{3-12}$ cycloalkyloxy, $C_{3-12}$ cycloalkylacyl, $C_{6-20}$ aryl, $C_{7-20}$ aralkyl and $C_{7-20}$ alkylaryl may be further substituted by halogen, nitro or cyano; provided that at least one of $R_1$, $R_2$, $R_3$ and $R_4$ is not hydrogen;
pyridazine derivative of formula (III):

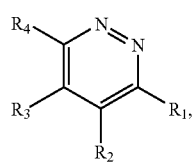

(III)

wherein $R_1$, $R_2$, $R_3$ and $R_4$ are independently selected from the group consisting of hydrogen, halogen, nitro, cyano, amino, $C_{1-6}$ alkylamino, $C_{1-12}$ alkyl, $C_{1-12}$ alkoxy, $C_{1-12}$ alkanoyl, $C_{3-12}$ cycloalkyl, $C_{3-12}$ cycloalkyloxy, $C_{3-12}$ cycloalkylacyl, $C_{6-20}$ aryl, $C_{7-20}$ aralkyl and $C_{7-20}$ alkylaryl; wherein $C_{1-6}$ allylamino, $C_{1-12}$ alkyl, $C_{1-12}$ alkoxy, $C_{1-12}$ alkanoyl, $C_{3-12}$ cycloalkyl, $C_{3-12}$ cycloalkyloxy, $C_{3-12}$ cycloalkylacyl, $C_{6-12}$ aryl, $C_{7-20}$ aralkyl and $C_{7-20}$ alkylaryl may be further substituted by halogen, nitro or cyano.

2. The process according to claim 1, wherein the imidazole derivative of formula (I) is selected from the group consisting of 2-methylimidazole, 1-methylimidazole, N-acetylimidazole, 2-isopropylimidazole, 1-(4-nitrophenyl)imidazole and 4,5-diphenylimidazole.

3. The process according to claim 1, wherein the pyridazine derivative of formula (III) is an unsubstituted pyridazine.

4. The process according to claim 1, wherein the metal halide is selected from the group consisting of cupric halide and cuprous halide.

5. The process according to claim 1, wherein the metal halide as catalyst has a concentration of 1 to 50000 ppm.

6. The process according to claim 1, wherein the molar ratio of the metal halide catalyst to the auxiliary catalyst is in the range of 10:1 to 1:10.

7. The process according to claim 6, wherein the molar ratio of the metal halide catalyst to the auxiliary catalyst is in the range of 5:1 to 1:5.

8. The process according to claim 1, wherein the alcohol is methanol.

9. The process according to claim 1, wherein the oxidative carbonylation of the alcohol is performed at a temperature of 60 to 200° C.

10. The process according to claim 9, wherein the oxidative carbonylation of the alcohol is performed at a temperature of 90 to 180° C.

11. The process according to claim 1, wherein the oxidative carbonylation of the alcohol is performed at a pressure of 15 to 40 kg/cm$^2$.

12. The process according to claim 11, wherein the oxidative carbonylation of the alcohol is performed at a pressure of 20 to 30 kg/cm$^2$.

* * * * *